United States Patent
Sabina et al.

(10) Patent No.: US 9,862,988 B2
(45) Date of Patent: *Jan. 9, 2018

(54) METHODS AND KITS FOR BREAKING EMULSIONS

(71) Applicant: LIFE TECHNOLOGIES CORPORATION, Carlsbad, CA (US)

(72) Inventors: Jeffrey Sabina, North Haven, CT (US); Ilya Zlatkovsky, San Francisco, CA (US); Rachel Kasinskas, Amesbury, MA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/449,192

(22) Filed: Mar. 3, 2017

(65) Prior Publication Data

US 2017/0175171 A1    Jun. 22, 2017

Related U.S. Application Data

(62) Division of application No. 14/110,695, filed as application No. PCT/US2012/032425 on Apr. 5, 2012, now Pat. No. 9,617,296.

(60) Provisional application No. 61/473,314, filed on Apr. 8, 2011.

(51) Int. Cl.
*C12Q 1/68* (2006.01)
*G01N 1/40* (2006.01)

(52) U.S. Cl.
CPC ......... *C12Q 1/6806* (2013.01); *C12Q 1/6874* (2013.01); *G01N 1/4055* (2013.01)

(58) Field of Classification Search
None
See application file for complete search history.

(56) References Cited

FOREIGN PATENT DOCUMENTS

WO    WO-2010/117461    10/2010

OTHER PUBLICATIONS

Anonymous, "DNA Sequencing Reaction Clean-up using Phenol and Butanol", Retrieved from the internet: URL:http://www.nucleics.com/DNA_sequencing_support/dna-sequencing-cleanup-protocol.html, XP002678647, Oct. 25, 2010, 1-3.
PCT/US2012/032425, International Preliminary Report on Patentability dated Oct. 17, 2013, 1-10.
PCT/US2012/032425, International Search Report and Written Opinion dated Jul. 13, 2012, 1-10.
Roboklon Detail Manual, "Micellula DNA Emulsion and Purification Kit", Version 1.1.0, Retrieved from the Internet: URL:http://www.roboklon.com/pdf/196_det_en.pdf, Oct. 2013, 1-20.
Roboklon Quick Manual, "Micellula DNA Emulsion and Purification Kit", Retrieved from the Internet: URL:http://www.roboklon.de/pdf/196_en.pdf, Jul. 10, 2010, 1.

*Primary Examiner* — Alicia L Otton

(57) ABSTRACT

The disclosure relates generally to methods, kits and systems for extracting biomolecules from a water-in-oil emulsion, including breaking a water-in-oil emulsion comprising a plurality of aqueous droplets in a continuous hydrophobic fraction using a breaking solution to produce a resulting reaction mixture containing one or more biomolecules and manipulating the resulting reaction mixture to form at least two phases, where one of the phases includes an aqueous phase containing the one or more biomolecules.

16 Claims, No Drawings

METHODS AND KITS FOR BREAKING EMULSIONS

CROSS-REFERENCE TO RELATED APPLICATIONS

This application is a Divisional application of U.S. application Ser. No. 14/110,695, filed Oct. 8, 2013, which is a U.S. national stage application claiming priority to International Application No. PCT/US2012/032425, filed Apr. 5, 2012, which claims priority to U.S. Provisional Patent Application No. 61/473,314, filed Apr. 8, 2011, entitled "METHODS AND KITS FOR BREAKING EMULSIONS" which is hereby incorporated by reference in its entirety.

TECHNICAL FIELD

In some embodiments, the disclosure relates generally to methods, compositions and systems for breaking water-in-oil emulsions comprising a continuous hydrophobic phase, in which a discontinuous aqueous phase is dispersed. In particular, methods for breaking emulsions providing greater ease of performance and better separation of phases are disclosed.

BACKGROUND

Emulsions are typically systems containing at least two immiscible (or substantially immiscible) liquids. Generally, at least one liquid serves as a dispersion phase, the phase dispersed as droplets; whereas at least one other liquid serves as the dispersion medium which is the phase that the droplets are dispersed in. Typical examples include water-in-oil or oil-in-water emulsions. An emulsion is typically a thermodynamically unstable mixture that tends to stay emulsified for a limited time. For example, coalescence occurs when droplets form together into larger droplets and generally indicates increased instability of an emulsion. Creaming occurs when one of the liquids migrates to the top of the emulsion (depending on density), and can sometimes look milky or creamy in appearance.

Emulsions are widely used in biological applications involving nucleic acid manipulation. For example, water-in-oil (w/o) emulsions including a continuous phase of water-immiscible liquid (e.g., oils, organic solvents) in which a discontinuous aqueous phase is dispersed are well known in the field of emulsion PCR. Emulsion PCR generally uses a water-in-oil emulsion, where the oil serves as the dispersion medium while the aqueous phase serves as the dispersion phase. During emulsion PCR, different biomolecules, e.g., proteins or nucleic acid templates, can be individually isolated within the aqueous droplets of the emulsion, with the oil phase acting as a barrier that physically compartmentalizes the templates from each other. Following the desired manipulation (e.g., amplification, expression, cleavage, etc), it is frequently desirable to disrupt or "break" the emulsion to recover the biomolecules from the emulsion. Classical methods of breaking such water-in-oil emulsions including biomolecules in the aqueous phase involve repeated rounds of extraction with organic solvents, such as water-saturated ether. See, e.g., Dressman et al., "Transforming single DNA molecules into fluorescent magnetic particles for detection and enumeration of genetic variation" Proc. Natl. Acad. Sci. 100(15):8817-8822 (2003); Ghadessy et al., "Directed evolution of polymerase function by compartmentalized self-replication", Proc. Natl. Acad. Sci. 98(8):4552-4557 (2000); Tawfik & Griffiths, "Man-made cell-like compartments for molecular evolution" Nat. Biotech. 16(7):652-656 (1998); Williams et al., "Amplification of complex gene libraries by emulsion PCR" Nat. Meth. 3(7):545-550 (2006). Such methods can be time-consuming, labor-intensive and costly.

Several biological applications also involve manipulation of nucleic acid molecules attached to supports. For example, several next-generation sequencing methods involve amplification and/or analysis of nucleic acid libraries, where individual members of the libraries are attached to particles. For such applications, it can be useful to obtain relatively accurate measure of the number of particles within a sample, as well as of the number of particles that are attached to particular nucleic acid sequences. For example, in methods involving extension of primers attached to particles, it can be useful to measure the number of particles including extended primers attached thereto (thereby gaining an indication of the efficiency of the primer extension reaction). Traditional methods of analyzing nucleic acid populations attached to particles involve individual assessment of one or more particles. For example, particle concentration is frequently estimated by counting of individual particles via flow cytometry, a costly and time consuming process. Similarly, the amount of particles including extended primers is typically assessed via hybridization of the particles to sequence-specific probes that hybridize selectively to extended portions of the primer, and visualizing such particles under the microscope to determine how many particles are hybridized to the sequence-specific probe. There is therefore a need for improved methods, compositions and systems that allow rapid, simple and inexpensive breaking of water-in-oil emulsions including biomolecules dispersed in the aqueous phase without significantly denaturing or otherwise disrupting the biomolecules or impairing their ability to participate in downstream manipulations such as nucleic acid sequencing, enzymatic reactions and the like.

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

SUMMARY

In some embodiments, the disclosure relates generally to methods, compositions, systems and kits for breaking a water-in-oil emulsion. In some embodiments, the method (as well as related compositions, systems and kits using the disclosed methods) includes obtaining a first emulsion including a continuous hydrophobic fraction and a discontinuous aqueous fraction, the aqueous fraction having one or more biomolecules dispersed therein, breaking the first emulsion by contacting the first emulsion with a breaking solution including a second emulsion, where the second emulsion includes a discontinuous phase of organic extraction solvent dispersed in a continuous aqueous phase and centrifuging to separate the phases of the resulting mixture. In some embodiments, the water-in-oil emulsion is a stable emulsion. Optionally, the aqueous fraction having one or more biomolecules dispersed therein can include one or more polynucleotides or polypeptides. In some embodiments, the polynucleotide can include a single-stranded or double-stranded polynucleotide. In some embodiments, the polypeptide can include an enzyme, antigen, hormone or antibody. In some embodiments, the one or more biomolecules can include RNA, mRNA, cDNA, DNA or genomic DNA. In some embodiments, the breaking solution can be formed by emulsifying an organic extraction solvent in an aqueous phase. In some embodiments, the organic extraction solvent can include butanol, octanol, hexanol or chloroform. In some embodiments, the aqueous phase used to emulsify the organic extraction solvent can include sodium dodecyl sulfate, phosphate buffered saline or saline-sodium citrate. In some embodiments, the continuous hydrophobic fraction includes oil. In some embodiments, the oil includes mineral oil, silicone based oil or fluorinated oil. In some embodiments, the breaking solution can further include an inorganic salt. The inorganic salt can optionally include potassium chloride, sodium chloride, lithium chloride, $Na_2SO_4$, potassium carbonate and ammonium sulfate. In some embodiments, the inorganic salt can be included in the aqueous phase of the breaking solution, prior to forming the breaking solution. Optionally, the method can further include enriching one or more of the biomolecules prior to centrifugation. In some embodiments, enriching can include isolating or capturing one or more of the biomolecules with a bead or particle. In some embodiments, one or more of the biomolecules present in the aqueous phase can be immobilized on a bead or particle. In some embodiments, the method can further include isolating or purifying one or more of the biomolecules from the separated phases. Optionally, the method can further include performing nucleic acid sequencing on one or more of the biomolecules.

In some embodiments, the disclosure generally relates to methods, systems, kits and compositions for extracting biomolecules from a water-in-oil emulsion. In some embodiments, the method (as well as related systems, kits and compositions using the disclosed methods) includes breaking a water-in-oil emulsion comprising a plurality of aqueous droplets in a continuous hydrophobic fraction using a breaking solution to produce a resulting reaction mixture containing one or more biomolecules and manipulating the resulting reaction mixture to form at least two phases, where one of the phases includes an aqueous phase containing the one or more biomolecules. In some embodiments, the water-in-oil emulsion is a stable emulsion. In some embodiments, the method includes a plurality of aqueous droplets having one or more biomolecules. In some embodiments, the method can further include recovering one or more of the biomolecules from the aqueous phase containing the one or more biomolecules. In some embodiments, the method can further include isolating or purifying one or more of the biomolecules extracted from the water-in-oil emulsion. Optionally, the method can include nucleic acid sequencing or protein expression of one or more of the biomolecules extracted from the water-in-oil emulsion. In some embodiments, the aqueous phase having one or more biomolecules can include one or more polynucleotides or polypeptides. In some embodiments, the polynucleotide can include a single-stranded or double-stranded polynucleotide. In some embodiments, the polypeptide can include an enzyme, antigen, hormone or antibody. In some embodiments, the one or more biomolecules can include RNA, mRNA, cDNA, DNA or genomic DNA. In some embodiments, the extracting can include breaking a water-in-oil emulsion using a breaking solution, where the breaking solution can be formed by emulsifying an organic extraction solvent in an aqueous phase. In some embodiments, the organic extraction solvent can include butanol, octanol, hexanol or chloroform. In some embodiments, the aqueous phase used to emulsify the organic extraction solvent can include sodium dodecyl sulfate, phosphate buffered saline or saline-sodium citrate. In some embodiments, the continuous hydrophobic fraction includes oil. In some embodiments, the oil includes mineral oil, silicone based oil or fluorinated oil. In some embodiments, the breaking solution can further include an inorganic salt. The inorganic salt can optionally include potassium chloride, sodium chloride, lithium chloride, $Na_2SO_4$, potassium carbonate and ammonium sulfate. Optionally, the aqueous phase used to form the breaking solution can include an inorganic salt prior to forming the breaking solution. The manipulating of the resulting reaction mixture can include any applicable means to form at least two phases, where one of the phases includes an aqueous phase containing the one or more biomolecules. In some embodiments, the manipulating can include mechanical means such as centrifuging or vortexing.

In some embodiments, the disclosure relates generally to kits (as well as related methods, systems and compositions using the disclosed kits) for extracting one or more biomolecules from a water-in-oil emulsion. In some embodiments, the kits include a breaking solution, or reagents for forming a breaking solution where the reagents include an organic extraction solvent emulsified in an aqueous phase, and instructions for performing the extraction of one or more biomolecules from the water-in-oil emulsion. In some embodiments, the kits include other consumables such as tubes, plates, vials for practicing the methods disclosed herein. In some embodiments, the kits can include a breaking solution, where the organic extraction solvent is optionally butanol, octanol, hexanol or chloroform. In some embodiments, the breaking solution is formed by emulsifying the organic extraction solvent in an aqueous phase. Optionally, the aqueous phase includes sodium dodecyl sulfate or phosphate buffered saline. In some embodiments, the one or more biomolecules can include a plurality of different biomolecules or a plurality of the same biomolecule in the water-in-oil emulsion. In some embodiments, the kit can include additional components. In some embodiments the additional components can include components sufficient to perform nucleic acid sequencing on the one or more biomolecules. In some embodiments, the kit can further include a polymerase, dATP, dTTP, dGTP, dCTP and cations, such as magnesium and manganese. In some embodiments, the kit can include one or more preservatives or adjuvants.

In some embodiments, the disclosure relates generally to systems (as well as related methods, kits and compositions using the disclosed systems) for recovering one or more biomolecules from a water-in-oil emulsion. In some embodiments, the system includes an automated platform or partially automated platform for performing any one or more steps of the methods disclosed herein. In some embodiments, the system includes an automated platform or partially automated platform for performing any one of the methods disclosed herein. In some embodiments, the system for recovering one or more biomolecules from a water-in-oil emulsion can include an automated system capable of breaking a water-in-oil emulsion. In some embodiments, the system for recovering one or more biomolecules from a water-in-oil emulsion can include an automated system capable of disrupting a water-in-oil emulsion. In some embodiments, the system includes an automated platform with a reservoir containing a breaking solution, and contacting the breaking solution with the water-in-oil emulsion to form a resulting reaction mixture. In some embodiments, the system includes a centrifugal module for separating the resulting reaction mixture into at least two phases, where one of the phases includes an aqueous phase having one or more of the biomolecules from the water-in-oil emulsion. In some embodiments, the system can further include an external computer component. Optionally, the computer component can execute software, firmware or instructionally control the automated platform to recover one or more biomolecules from the water-in-oil emulsion. In some embodiments, the computer component can be operatively connected to other computers or servers that can enable remote operation of the automated platform.

In some embodiments, a system for recovering one or more biomolecules from a water-in-oil emulsion can include an automated platform that may include contacting a breaking solution with a water-in-oil emulsion, and is capable of manipulating the resulting reaction mixture to separate phases. In some embodiments, the system is capable of manipulating the resulting reaction mixture to form at least two phases, where one of the phases is an aqueous phase containing the one or more biomolecules of the water-in-oil emulsion. In some embodiments, the systems disclosed can provide as an output, a continuous aqueous phase containing one or more biomolecules released from the water-in-oil emulsion. In some embodiments, the aqueous phase containing the one or more biomolecules can be further isolated or purified. In some embodiments, isolated or purified biomolecules obtained using the disclosed methods, kits, or systems can be used in any applicable downstream process or method.

DETAILED DESCRIPTION

As used herein, "amplify", "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the first nucleic acid molecule. The first nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the first nucleic acid molecule. Amplification optionally includes linear or exponential replication of a nucleic acid molecule. In some embodiments, such amplification is performed using isothermal conditions; in other embodiments, such amplification can include thermocycling. In some embodiments, "amplification" includes amplification of at least some portion of DNA- and RNA-based nucleic acids alone, or in combination. The amplification reaction can include single or double-stranded nucleic acid substrates and can further including any of the amplification processes known to one of ordinary skill in the art. In some embodiments, the amplification reaction includes polymerase chain reaction (PCR). In exemplary embodiments, the amplification reaction can include clonal amplification of one or more nucleic acid templates.

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocyling conditions, or a combination of isothermal and themocycling conditions. In some embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more different nucleic acid sequences, or to amplify an amplified nucleic acid sequence ligated to one or more adapters, or attached to a support, e.g., a particle or bead. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{++}$ or $Mn^{++}$ (e.g., $MgCl_2$, etc) and can also include various modifiers of ionic strength. In some embodiments, amplification occurs within discrete aqueous droplets or within a discontinuous aqueous phase. In various embodiments, a single nucleic acid sequence to be amplified can be present within the aqueous phase or aqueous droplet, and is optionally, attached to a support, e.g., a bead or particle.

As used herein "amplicon" and its derivatives are used in the broadest sense to include selected amplification products, such as those produced from a polymerase chain reaction or ligase chain reaction technique. In an exemplary embodiment, amplicons can be prepared using Ion Torrent Ampliseq™ technology, such as the Ion Torrent Ampliseq™ Cancer Panel (Life Technologies, Part No. 4472395). In other embodiments, amplicons can be prepared using a variety of library preparation techniques known to one of ordinary skill in the art and/or commercially available kits. In an exemplary embodiment, a library fragment kit can be used with or without barcodes, such as the Ion Express Fragment Library Kit (Life Technologies, Part No. 4468987) or the Ion Fragment Library Kit (Life Technologies, Part No. 4466464) in the presence or absence of the Ion DNA barcoding 1-16 Kit (Life Technologies, Part No. 4468654).

As termed herein "genomic library" and its derivatives, generally refers to a collection of nucleic acid molecules derived from and/or representing an entire genome of an organism or individual.

As defined herein, "sample" and its derivatives, is used in its broadest sense and includes any specimen, culture and the like that is suspected of including a nucleic acid sequence to be amplified. In some embodiments, the sample comprises DNA, cDNA, RNA, PNA, LNA, chimeric, hybrid, or multiplex-forms of nucleic acids. The sample can include any biological, clinical, surgical, agricultural, atmospheric or aquatic-based specimen containing one or more nucleic acids. The term also includes any isolated nucleic acid sample such a genomic DNA, needle biopsy DNA, laser-capture DNA, tumor DNA, fresh-frozen or formalin-fixed paraffin-embedded nucleic acid specimen.

As used herein, "contacting" and its derivatives, when used in reference to two or more components, refers generally to any process whereby the approach, proximity, mixture or commingling of the referenced components is promoted or achieved without necessarily requiring physical contact of such components, and includes mixing of solutions containing any one or more of the referenced components with each other. The referenced components may be contacted in any particular order or combination and the particular order of recitation of components is not limiting. For example, "contacting A with B and C" encompasses embodiments where A is first contacted with B then C, as well as embodiments where C is contacted with A then B, as well as embodiments where a mixture of A and C is contacted with B, and the like. Furthermore, such contacting does not necessarily require that the end result of the contacting process be a mixture including all of the recited components, as long as at some point during the contacting process all of the referenced components are simultaneously present or simultaneously included in the same mixture or solution. For example, "contacting A with B and C" can include embodiments wherein C is first contacted with A to form a first mixture, which first mixture is then contacted with B to form a second mixture, following which C is removed from the second mixture; optionally A can then also be removed, leaving only B. Where one or more of the referenced components includes a plurality (e.g., "one or more biomolecules"), then each member of the plurality can be viewed as an individual component of the contacting process, such that the contacting can include contacting of any one or more members of the plurality with any other member of the plurality and/or with any other referenced component (e.g., some but not all of the plurality of biomolecules can be contacted with a breaking solution, then a recovery solution, and then with other members of the plurality of biomolecules) in any order or combination.

The term "extension" and its variants, as used herein, when used in reference to a given primer, comprises any in vivo or in vitro enzymatic activity characteristic of a given polymerase that relates to polymerization of one or more nucleotides onto an end of an existing nucleic acid molecule. Typically but not necessarily such primer extension occurs in a template-dependent fashion; during template-dependent extension, the order and selection of bases is driven by established base pairing rules, which can include Watson-Crick type base pairing rules or alternatively (and especially in the case of extension reactions involving nucleotide analogs) by some other type of base pairing paradigm. In one non-limiting example, extension occurs via polymerization of nucleotides on the 3'OH end of the nucleic acid molecule by the polymerase.

As used herein, "polymerase" and its derivatives, generally refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity.

As used herein "water-in-oil emulsion" and its derivatives, generally refers to an emulsion comprising a continuous hydrophobic fraction and a discontinuous aqueous fraction, where the aqueous fraction includes one or more biomolecules dispersed therein. Typically, the discontinuous aqueous fraction comprises a plurality of hydrophilic components that are also referred to herein as "aqueous droplets". Conversely, an "oil-in-water" emulsion generally refers to an emulsion comprising a continuous aqueous phase and a discontinuous hydrophobic phase. In some embodiments, the aqueous phase of a water-in-oil emulsion includes one or more biomolecules. In some embodiments, the discontinuous aqueous phase of an emulsion can be composed of a high density of aqueous droplets. In some embodiments, one or more aqueous droplets can include one, two, three, four, five, six, seven, eight, nine, ten, or more different biomolecules.

As used herein "stable emulsion" and its derivatives generally refer to an emulsion that does not substantially degrade, collapse or in which the hydrophilic compartments do not substantially coalesce under amplification conditions. Therefore, in various exemplary embodiments, a water-in-oil emulsion as defined here can be suitable for carrying out reactions at varying temperatures (e.g., thermocycling, such as, PCR), and other conditions (e.g., pH, ionic strength, hybridization conditions, etc.), and in the presence of various reaction components (e.g., nucleic acids, proteins, enzymes, catalysts, co-factors, intermediates, products, by-products, labels, microparticles, etc.).

As used herein "hydrophobic fraction", "hydrophobic phase" and its derivatives, generally refers to a substance that is liquid at ambient temperatures and is hydrophobic but also soluble in organic solvents. In a non-limiting exemplary embodiment, a hydrophobic fraction includes oil.

As used herein "oil" and its derivatives, generally refers to a substance that is liquid at ambient temperature, is hydrophobic but also soluble in organic solvents. In a non-limiting exemplary embodiment, oil includes mineral oils, silicone-based oils or fluorinated oils. In some embodiments, the oil can be emulsion oil (sold as a component of Ion Torrent Template Preparation Kit (Life Technologies, Part No. 4469000)).

As used herein "breaking solution" and its derivatives, generally refers to a liquid at ambient temperatures that is sufficient (under appropriate reaction conditions, such as room temperature) to break or disrupt water-in-oil emulsions (i.e., a first emulsion). Typically, the breaking solution can be suitable for releasing biomolecules present in a discontinuous aqueous phase of the first emulsion into a resulting continuous aqueous phase. In some embodiments, the breaking solution can be formed by emulsifying an organic extraction solvent with an aqueous phase to form an emulsion (i.e., a second emulsion). In a non-limiting exemplary embodiment, an organic extraction solvent can include butanol, octanol, chloroform or hexanol. In some embodiments, the breaking solution formed by emulsifying an organic extraction solvent with an aqueous phase, can further include one or more inorganic salts. Optionally, an inorganic salt can be added to the aqueous phase prior to emulsifying the organic extraction solvent to form the breaking solution. In some embodiments, the inorganic salt can include potassium chloride, sodium chloride, lithium chloride, $Na_2SO_4$, potassium carbonate and ammonium sulfate.

In some embodiments, releasing biomolecules from a stable emulsion or a water-in-oil emulsion can be performed with a single aliquot or single application of the breaking solution. In some aspects, the methods, kits, compositions and systems disclosed herein negate the need for repeated organic solvent extractions to release biomolecules from stable or water-in-oil emulsions. Generally, contacting a breaking solution with a water-in-oil emulsion containing one or more nucleic acids or polypeptides in an aqueous phase results in release of said nucleic acids or polypeptides from the aqueous droplets of the discontinuous aqueous phase, and the formation of a resulting continuous aqueous phase containing the released nucleic acids or polypeptides. In some embodiments, biomolecules released by contacting the water-in-oil emulsion with the breaking solution can be recovered using any applicable method known to one of skill in the art. In various exemplary embodiments, mechanical or filtering means can be used to recover biomolecules released from a stable or water-in-oil emulsion. For example vortexing, centrifuging and/or filtering can be used to recover biomolecules from the continuous aqueous phase after contacting a water-in-oil emulsion with a breaking solution. In some embodiments, biomolecules can be recovered after contacting a stable emulsion (containing one or more biomolecules) with a breaking solution by more than one form of manipulation. For example, biomolecules released from a first emulsion by contacting the first emulsion with a breaking solution can be further manipulated for example by isolating, extracting and/or purifying the biomolecules using one or more methods known to one of ordinary skill in the art. For example, in some embodiments, biomolecules released after contact with a breaking solution can be isolated or extracted from the resulting continuous aqueous phase using a pipette, centrifuge or vacuum. The isolated or extracted biomolecules can, for example, undergo a recovery treatment to stabilize, de-salt or improve the purity of the isolated or extracted biomolecules. For example, in some embodiments isolated or extracted biomolecules can be treated with a recovery solution and/or a wash solution. In some embodiments, the isolated or extracted biomolecules can be filtered to purify the isolated or extracted biomolecules. In yet another embodiment, the isolated or extracted biomolecules can be de-salted or denatured for use in any applicable downstream process, such as enzymatic reactions and nucleic acid sequencing. In some aspects, it may be useful to denature nucleic acids that are attached or immobilized on a support prior to performing a downstream process such as nucleic acid sequencing.

As used herein "isolating" and "extracting" are used interchangeably and generally refer to a process by which one or more biomolecules (e.g., nucleic acids or polypeptides) are separated from other components, compounds, phases or solvents of a particular reaction mixture. Generally, isolating or extracting refers to a process by which the intended biomolecules are separated from other biological or chemical compounds in a reaction mixture. Any applicable means to perform the extraction or isolation process are contemplated by the instant application. In an exemplary embodiment, biomolecules can be isolated or extracted from a reaction mixture by contacting the reaction mixture with a recovery solution, wash solution and/or denaturing solution. In some embodiments, biomolecules can be isolated from a reaction mixture using mechanical means such as vortexing or centrifuging. In some embodiments, isolating or extracting can include a combination of recovery, wash or denaturation solutions in conjunction with one or more mechanical means. In another embodiment, extracting can include filtering the reaction mixture, for example to retain the intended biomolecules of the reaction mixture while discarding other components of the reaction mixture. Filtering can include columns of various sorts, such as column chromatography, ion exchange chromatography, centrifugal filters, microfilters, membrane filtering, and the like. In some embodiments, the isolating or extracting refers to the isolation or extraction of intended DNA and/or polypeptides. In some embodiments, filtering can include size-specific filtering such as HPLC, gel electrophoresis, size-specific spin columns and the like. In some embodiments, the isolating includes removal of cellular debris, proteases or other nonspecific components from the reaction mixture to retain intended biomolecules. In some embodiments, isolating or extracting can include the removal of lipids, organic or inorganic compounds from a reaction mixture that can interfere with downstream processing such a nucleic acid sequencing or protein expression.

As used herein "recovery solution" and its derivatives, generally refers to a liquid at ambient temperatures that is sufficient (under appropriate reaction conditions e.g., room temperature) to isolate or extract biomolecules obtained in a continuous aqueous phase after contacting a breaking solution with a stable water-in-oil emulsion. In some embodiments, the recovery solution can include a detergent or surfactant. In some embodiments, the recovery solution is an aqueous solution that includes sodium dodecyl sulfate (SDS) or saline-sodium citrate (SSC). In some embodiments, the recovery solution includes about 0.01% to about 5% SDS or SSC. In some embodiments, the recovery solution includes about 0.05% to about 1% SDS or SSC. In some embodiments the recovery solution includes phosphate buffered saline (PBS). In one exemplary embodiment, the recovery solution can include 1×PBS. In some embodiments, biomolecules treated with a recovery solution can be further purified using a wash solution and/or a denaturation solution. In some embodiments, biomolecules treated with a recovery solution can be further stabilized, de-salted or purified using any method known to one of ordinary skill in the art. Generally, the recovery solution can be applied to the continuous aqueous phase after treating a stable water-in-oil emulsion with a breaking solution. Typically, after addition of the recovery solution to the continuous aqueous phase the resulting reaction mixture is manipulated, for example, by mechanical means such as vortexing and/or centrifuging to assist in the recovery of biomolecules from the continuous aqueous phase. It is contemplated that other means of manipulation are applicable as would be readily determined by one of ordinary skill in the art. For example, additional surfactants or stabilizing agents may be employed in some embodiments to promote additional stability of the recovered biomolecules. In an exemplary embodiment, the recovery solution can include the Ion Torrent Recovery Solution (Life Technologies, Part No. 4468998, sold as a component of the Ion Template Solutions Kit (Life Technologies).

As used herein "wash solution" and its derivatives, generally refers to a solution that can assist in the purification of biomolecules after the application of a recovery solution to an aqueous solution containing isolated biomolecules from a stable water-in-oil emulsion. In some embodiments, the wash solution can be used to remove residual oil. In some embodiments, the wash solution can include a detergent or surfactant. In some embodiments, the wash solution can include Triton X-100 (Octylphenol ethylene oxide condensate). In some embodiments, the wash solution can include about 0.01% to about 5% Triton X-100. In some embodiments, the wash solution can include about 0.05% to about 1% Triton-X. In some embodiments, the wash solution can include Tris-HC1 or Tris-EDTA. In some embodiments, the wash solution can lower the amount of bead or particle clumping as compared to a similarly prepared reaction mixture that is not treated with the wash solution. In an exemplary embodiment, the wash solution can include the Ion Torrent Wash Solution (Life Technologies, Part No. 4468998, sold as a component of the Ion Template Solutions Kit (Life Technologies). In some embodiments, the wash solution and/or the recovery solution can contain Tris-EDTA (TE). In some embodiments, the wash solution and/or the recovery solution can include 1×TE.

As used herein "denaturation solution" and its derivatives, generally refers to a solution that can denature polypeptides or nucleic acids. For example, a denaturation solution for nucleic acids may separate a duplex structure into single strands of DNA or denature a nucleic acid or polypeptide from a support, such as a bead or particle. In some embodiments, a denaturation solution can be sufficient to denature polypeptides present in a solution when intending to recover only DNA or RNA molecules. In some embodiments, the denaturation solution can include Tween 20 (polysorbate 20) and/or sodium hydroxide. In some embodiments, the denaturation solution can include about 0.01% to about 5% Tween 20. In some embodiments, the denaturation solution can include about 0.05% to about 1% Tween 20. In some embodiments, the denaturation solution can include about 100 mM to about 400 mM NaOH.

As used herein "support" and its derivatives, generally refers to any support to which one or more nucleic acids or polypeptides can be linked, attached or immobilized. The linkage, attachment or immobilization of polypeptides or nucleic acids can be through any form or means known to one of ordinary skill in the art. For example, in some embodiments, the support can include beads suitable for the capture of nucleic acids or polypeptides. In a non-limiting example, beads can include magnetic, paramagnetic or superparamagentic capture beads. In another non-limiting example, polypeptide or nucleic acid beads can include those prepared and commercially available from Dynal Biotech and Life Technologies (CA). In an exemplary embodiment, beads can include biotin-streptavidin beads. In some embodiments, the support can be a particle such as a microsphere. In some embodiments, the support can be a fluorescent or non-fluorescent microsphere. In some embodiments, the particle can include an Ion Sphere™ Particle (Life Technologies, Part No. 4468999 sold as a component of Ion Torrent Reagents Kit). In some embodiments, the support can include a particle coated with one or more primers that are substantially complementary (or complementary) to one or more nucleic acids to be attached to the particle. In some embodiments, the support can be a solid support (e.g., a slide, glass plate, channel, groove, wafer and the like). In some embodiments, the support can be coated or layered with one or more nucleic acid primers or probes that are substantially complementary (or complementary) to one or more nucleic acids to be attached to the support. In some embodiments, the support can include hydrogel particles suitable for nucleic acid or protein attachment, linkage or immobilization. In some embodiments, hydrogel particles can include polyethylene glycol hydrogel particles. In some embodiments, particles can include permeable particles. In some embodiments, the support can include one or more types of support.

As used herein "biomolecules" and derivatives, generally refers to any biomolecule that can be compartmentalized in the aqueous phase of a water-in-oil or oil-in-water emulsion. In exemplary embodiments, biomolecules can include one or more polypeptides or polynucleotides. In some embodiments, biomolecules can include a plurality of nucleic acid templates or nucleic acid libraries such as cDNA libraries or genomic DNA libraries. In some embodiments, a biomolecule can include a single-stranded or double-stranded polynucleotide, or a combination of both. In some embodiments, the biomolecules can include one or more RNA, DNA, cDNA, mRNA or genomic DNA. In some embodiments, biomolecules include one or more polypeptides, for example an enzyme, an antigen, a hormone or an antibody.

As used herein "breaking an emulsion" or "disrupting an emulsion" and its derivatives, generally refers to a process in which a stable emulsion or a water-in-oil emulsion containing an aqueous phase having one or more biomolecules dispersed within a plurality of aqueous droplets is broken or disrupted such that the biomolecules present in the aqueous phase droplets are released into a resulting continuous aqueous phase. In some embodiments, the plurality of aqueous droplets can contain a single biomolecule, e.g., a nucleic acid template. In some embodiments, aqueous droplets can include different biomolecules in different aqueous droplets. In this aspect, breaking the emulsion results in the release of the plurality of biomolecules into the continuous aqueous phase. Generally, contacting aqueous droplets of a stable water-in-oil emulsion with a breaking solution as described herein can result in the release of the plurality of biomolecules into the resulting reaction mixture (i.e., continuous aqueous phase).

The practice of the present subject matter may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation of synthetic polynucleotides, polymerization techniques, chemical and physical analysis of polymer particles, nucleic acid sequencing and analysis, protein expression, plasmid construction, and the like. Specific illustrations of suitable techniques can be used by reference to the example herein below. Other equivalent conventional procedures can also be used. Such conventional techniques and descriptions can be found in standard laboratory manuals such as *Genome Analysis: A Laboratory Manual Series* (Vols. I-IV), *PCR Primer: A Laboratory Manual, and Molecular Cloning: A Laboratory Manual* (all from Cold Spring Harbor Laboratory Press), Hermanson, Bioconjugate Techniques, Second Edition (Academic Press, 2008); Merkus, Particle Size Measurements (Springer, 2009); Rubinstein and Colby, Polymer Physics (Oxford University Press, 2003); and the like.

In some embodiments, the disclosure relates generally to methods, compositions, systems, apparatuses and kits involving manipulation of biomolecules (e.g., nucleic acids, proteins) in water-in-oil emulsions, comprising: obtaining a first emulsion including a continuous hydrophobic fraction and a discontinuous aqueous fraction, the aqueous fraction having one or more biomolecules dispersed therein; and breaking the first emulsion. In some embodiments, the first emulsion is disrupted with the breaking solution, thereby releasing the one or more biomolecules into a resulting continuous aqueous phase. In some embodiments, the breaking solution can include a second emulsion, where the second emulsion includes a discontinuous phase of organic extraction solvent dispersed in a continuous aqueous phase. In some embodiments, the first emulsion contacted with the breaking solution, including the second emulsion, is centrifuged to separate the phases of the resulting mixture.

In some embodiments, the disclosure relates generally to methods, compositions, systems and kits involving manipulation of nucleic acids or polypeptides in a stable emulsion comprising: obtaining a stable emulsion including a continuous hydrophobic fraction and a discontinuous aqueous fraction, the aqueous fraction having one or more biomolecules dispersed therein; and breaking the stable emulsion. In some embodiments, the stable emulsion is disrupted with the breaking solution, thereby releasing the one or more biomolecules into a resulting mixture. In some embodiments, the resulting mixture is centrifuged to separate the resulting phases.

In some embodiments, stable emulsions or water-in-oil emulsions can include a plurality of hydrophilic compartments also referred to as aqueous droplets. In some embodiments the mean diameter of hydrophilic compartments can include about 0.5 µm, 1 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 150 µm, 200 µm, 250 µm, 300 µm, 350 µm, 400 µm, 450 µm to about 500 µm. In various exemplary embodiments, the mean volume of hydrophilic compartments can be about 0.5 $\mu m^3$ to about 4,000,000 $\mu m^3$, from about 500 $\mu m^3$ to about 500,000 $\mu m^3$, from about 8,000 $\mu m^3$ to about 200,000 $\mu m^3$. However, larger and smaller hydrophilic compartments also can be contemplated. In some embodiments, the standard deviation in mean diameter or mean volume of hydrophilic compartments is generally less than 50%.

In some embodiments, aqueous droplets can be formed in a very high density enabling the breaking of a stable emulsion and recovery of biomolecules in a massively parallel way.

In some embodiments, the disclosure relates generally to methods, compositions, systems and kits involving manipulation of amplicons in a stable emulsion comprising: obtaining a stable emulsion including a continuous hydrophobic fraction and a discontinuous aqueous fraction, the aqueous fraction having one or more amplicons dispersed therein; and breaking the stable emulsion. In some embodiments, the stable emulsion is disrupted with the breaking solution, thereby releasing the one or more amplicons into a resulting continuous aqueous phase. In some embodiments, the released amplicons can be further isolated or purified, for example by centrifuging or filtering.

In some embodiments, an aqueous droplet can include one or more amplicons, for example, amplicons prepared from one or more commercially available kits, such as the Ion Ampliseq™ Cancer Panel (Life Technologies Part No. 4472395). Typically, in emulsion PCR, it is often useful to provide one amplicon per aqueous droplet.

In some embodiments, the disclosure relates generally to methods, compositions, systems and kits involving manipulation of genomic DNA libraries or cDNA libraries in water-in-oil emulsions, comprising: obtaining a first water-in-oil emulsion including a continuous hydrophobic fraction and a discontinuous aqueous fraction, the aqueous fraction having the genomic DNA or cDNA library dispersed therein; and breaking the first water-in-oil emulsion. In some embodiments, the first water-in-oil emulsion is contacted with a breaking solution including a second emulsion; and centrifuged to separate the phases of the resulting mixture.

In some embodiments, the breaking includes contacting the first emulsion with a breaking solution.

The breaking solution optionally includes an organic extraction solvent dispersed in an aqueous phase. In some embodiments, breaking the first emulsion having one or more biomolecules dispersed in a discontinuous aqueous fraction therein, and recovering the one or more biomolecules from the first emulsion treated with the breaking solution can be performed in a single administration of the breaking solution to the first emulsion. In some embodiments, the recovered biomolecules can optionally be extracted or isolated with a recovery solution and/or a wash solution. In some embodiments, the breaking solution when prepared as an emulsion, or the recovery solution can include one or more inorganic salts such as potassium chloride, sodium chloride, lithium chloride, $Na_2SO_4$, potassium carbonate, ammonium sulfate, and the like.

In some embodiments, the biomolecules can be selected from the group consisting of: polynucleotides and polypeptides. The polynucleotides can be single-stranded or double-stranded, and can include RNA, DNA, cDNA, mRNA, and the like. The polypeptides can optionally be selected from the group consisting of enzymes, antibodies, hormones and antigens.

In some embodiments, the breaking solution can include a second emulsion comprising a continuous aqueous phase and a discontinuous phase including the organic extraction solvent.

The organic extraction solvent can be optionally selected from the group consisting of: butanol, octanol, hexanol and chloroform.

The aqueous phase of the breaking solution can optionally include sodium dodecyl sulfate (SDS), Tris-EDTA (TE), phosphate buffered saline (PBS) and saline-sodium citrate (SSC).

In some embodiments, the disclosed methods can further include forming a breaking solution by emulsifying the organic extraction solvent in an aqueous phase.

In some embodiments, a method for breaking a water-in-oil emulsion including one or more biomolecules dispersed in an aqueous phase of the water-in-oil emulsion is provided, comprising: obtaining a first emulsion including a continuous hydrophobic fraction and a discontinuous aqueous fraction, the aqueous fraction having one or more biomolecules dispersed therein; breaking the first emulsion by contacting the first emulsion with a breaking solution including a second emulsion, where the second emulsion includes a discontinuous phase of organic extraction solvent dispersed in a continuous aqueous phase; and centrifuging to separate the phases of the resulting mixture.

In some embodiments, a method of extracting biomolecules from a water-in-oil emulsion is provided, comprising breaking a water-in-oil emulsion comprising a plurality of aqueous droplets in a continuous hydrophobic fraction using a breaking solution to produce a resulting reaction mixture containing one or more biomolecules, and manipulating the resulting reaction mixture to form at least two phases, wherein one of the phases includes an aqueous phase containing the one or more biomolecules.

In some embodiments, droplets within the discontinuous aqueous phase of a water-in-oil emulsion contain nucleic acids or polypeptides. In some embodiments, droplets contain different nucleic acid sequences or different polypeptides. In some embodiments, droplets contain a single nucleic acid sequence or single polypeptide. In some embodiments, applying the breaking solution to the first emulsion results in release of said nucleic acids or polypeptides from the aqueous droplets of the discontinuous phase, and the formation of a resulting continuous aqueous phase containing the multiple nucleic acids or polypeptides released from the aqueous droplets. In some embodiments, the biomolecules isolated or released by the breaking solution can be recovered using mechanical or filtering means, for example, vortexing, centrifugation and/or filtering. In some embodiments, the biomolecules released from the first emulsion can be recovered by any method known to those of ordinary skill in the art. In some embodiments, the biomolecules can be further purified, stabilized or de-salted using a recovery and/or wash solution. In some embodiments, the recovered biomolecules can be used in any applicable downstream process. In some aspects where the biomolecules are nucleic acids, the downstream processes can include without limitation, nucleic acid sequencing, targeted resequencing, genotyping analysis, mutation analysis, copy number variation assessment, allele frequency assessment, plasmid construction, cloning, and the like. In some aspects wherein the biomolecules are polypeptides, the downstream processes can include without limitation, protein cloning, protein expression and gene expression. In some aspects, biomolecules obtained using the methods, kits, and systems disclosed herein can be used in any applicable field of use. For example, nucleic acids obtained using the disclosed methods, system and kits can be used in forensic or human identification purposes. In another embodiment, nucleic acids obtained using the methods, systems and kits disclosed herein can be used for pathogenic, epidemiological or geographical migration studies. In yet another embodiment, the methods, kits and systems disclosed herein can be used to obtain nucleic acids that can be used to evaluate or detect variants in nucleic acid sequence by any method known in the art. In some embodiments, the evaluation of variants can include diagnostic or prognostic evaluation.

In some embodiments, the breaking solution includes an organic extraction solvent that is not water-saturated. In some aspects, the use of a non-water-saturated organic extraction solvent increases the stability of an emulsion formed by emulsifying an organic extraction solvent and an aqueous phase to form the breaking solution. Additionally, the use of a non-water-saturated organic extraction solvent removes a time-consuming and labor intensive step from the previously known emulsion breaking processes. Typically in the art, a water-saturated organic extraction solvent is prepared prior to performing an emulsion breaking method. In the present application, this would translate to i) preparing a water-saturated organic extraction solvent; and ii) using the water-saturated organic solvent to prepare a breaking solution (e.g., emulsifying a water-saturated organic solvent with an aqueous phase to form a breaking solution). Thus, the disclosed methods, systems and kits provide an improved method for breaking water-in-oil emulsions.

In some embodiments, the breaking solution can include one or more different organic extraction solvents. In some embodiments, a single application or single aliquot of a breaking solution to a first emulsion containing one or more biomolecules is sufficient to break the first emulsion and recover the one or more biomolecules from the first emulsion. Optionally, the recovered biomolecules from the first emulsion can be further isolated or purified with a recovery and/or wash solution. In some embodiments, the recovered or purified biomolecules can be used in any downstream method known to one of ordinary skill in the art. In a non-limiting example, the recovered or purified biomolecules can be used for directed evolution of polymerases, reverse-transcription PCR, nucleic acid sequencing, genotyping, haplotyping, mutation analysis, variant analysis, high-throughput screening of transcription-factor targets, plasmid construction, cloning, expression vectors and protein expression.

In some embodiments, the methods, kits and systems disclosed herein can be used to evaluate or detect variants in nucleic acid sequence by any method known to one or ordinary skill in the art. In one embodiment, biomolecules obtained after breaking a water-in-oil emulsion using the methods, systems and kits disclosed herein can be used in next generation sequencing systems. Exemplary next-generation sequencing systems include the Ion Torrent PGM™ sequencer (Life Technologies) and the Ion Torrent Proton™ Sequencer (Life Technologies), which are ion-based sequencing systems that sequence nucleic acid templates by detecting ions produced as a byproduct of nucleotide incorporation. Typically, hydrogen ions are released as byproducts of nucleotide incorporations occurring during template-dependent nucleic acid synthesis by a polymerase. The Ion Torrent PGM™ sequencer and Ion Proton™ Sequencer detect the nucleotide incorporations by detecting the hydrogen ion byproducts of the nucleotide incorporations. The Ion Torrent PGM™ sequencer and Ion Torrent Proton™ sequencer include a plurality of nucleic acid templates to be sequenced, each template disposed within a respective sequencing reaction well in an array. The wells of the array are each coupled to at least one ion sensor that can detect the release of $H^+$ ions or changes in solution pH produced as a byproduct of nucleotide incorporation. The ion sensor comprises a field effect transistor (FET) coupled to an ion-sensitive detection layer that can sense the presence of $H^+$ ions or changes in solution pH. The ion sensor provides output signals indicative of nucleotide incorporation which can be represented as voltage changes whose magnitude correlates with the $H^+$ ion concentration in a respective well or reaction chamber. Different nucleotide types are flowed serially into the reaction chamber, and are incorporated by the polymerase into an extending primer (or polymerization site) in an order determined by the sequence of the template. Each nucleotide incorporation is accompanied by the release of $H^+$ ions in the reaction well, along with a concomitant change in the localized pH. The release of $H^+$ ions is registered by the FET of the sensor, which produces signals indicating the occurrence of the nucleotide incorporation. Nucleotides that are not incorporated during a particular nucleotide flow will not produce signals. The amplitude of the signals from the FET may also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers permit the instrument to resolve the sequence of many nucleic acid templates simultaneously. Further details regarding the compositions, design and operation of the Ion Torrent PGM™ sequencer can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

In some embodiments, kits for performing extraction of biomolecules from a water-in-oil emulsion are provided that include a breaking solution, or reagents for forming a breaking solution and instructions for performing the extraction of biomolecules from the water-in-oil emulsion. In another embodiment, a kit is provided for obtaining one or more biomolecules from a water-in-oil emulsion, the kit having one or more reagents to disrupt a water-in-oil emulsion. In some embodiments, the kit includes a breaking solution, or reagents to form a breaking solution and instructions for doing the same. In some embodiments, kits include other consumables such as tubes, plates, vessels and/or chambers to perform extraction of biomolecules from water-in-oil emulsions. In some embodiments, kits for extracting biomolecules from a water-in-oil emulsion include an organic extraction solvent. In one embodiment, the kit can include one or more types of organic extraction solvent. In some embodiments, the organic extraction solvent can include butanol, octanol, hexanol or chloroform. In some embodiments, the kit can include an organic extraction solvent emulsified in an aqueous solution. In another embodiment, the kit can include an organic extraction solvent, an aqueous solution and instructions for forming a breaking solution that can be used to extract biomolecules from a water-in-oil emulsion. In some embodiments, the aqueous solution for forming a breaking solution may include SDS, PBS, TE or SSC.

In one embodiment, a system for recovering one or more biomolecules from a water-in-oil emulsion is provided herein. For example, a water-in-oil emulsion may be disrupted in an automated or partially automated fashion using an instrument configured to perform some or all of the necessary steps or functions. Examples of such instruments may include robotic platforms such as those available from Hamilton Robotics, Beckman Coulter, Caliper Life Sciences or Life Technologies. Further, such an instrument may be operatively linked to one or more external computer components that may for instance execute system software or firmware that may provide instructional control of one or more of the instruments or functions. The external computer may be additionally operatively connected to other computers or servers via a network that may enable remote operation of the instrument. In the present example, such an instrument or platform can include some or all of the components and characteristics of the embodiments generally described above.

In one embodiment, a system for recovering one or more biomolecules from a water-in-oil emulsion can include an automated platform that may include contacting a breaking solution with a water-in-oil emulsion, and is capable of manipulating the resulting reaction mixture to separate phases. In some embodiments, the system is capable of manipulating the resulting reaction mixture to form at least two phases, where one of the phases is an aqueous phase containing the one or more biomolecules.

In one embodiment, a system for recovering one or more biomolecules from a water-in-oil emulsion can include emulsifying an organic extraction solvent with an aqueous solution to form a breaking solution, and contacting the breaking solution with a water-in-oil emulsion. In a further aspect, the system may include a centrifugal module that can separate phases after contacting a water-in-oil emulsion with a breaking solution. In some embodiments, the breaking solution can include hexanol, butanol, octanol or chloroform. In another embodiment, the aqueous phase of the breaking solution can include SDS, PBS, TE or SSC. In some embodiments, the breaking solution when prepared as an emulsion can further include an inorganic salt. In some embodiments, the systems disclosed can provide (as an output) a continuous aqueous phase containing one or more biomolecules released from the water-in-oil emulsion. In some embodiments, the aqueous phase containing the one or more biomolecules can be further isolated or purified. In some embodiments, isolated or purified biomolecules obtained using the disclosed methods, kits, or systems can be used in any applicable downstream process or method. It will be readily apparent to one of ordinary skill in the art that the embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

EXAMPLES

Example 1: Breaking of Water-in-Oil Emulsions including Nucleic Acid Molecules in the Aqueous Phase Using A Breaking Solution Comprising an Emulsion of Butanol in Sodium Dodecyl Sulfate (SDS)

This example describes the breaking of a water-in-oil emulsion including amplified nucleic acid molecules in an aqueous phase, using a second emulsion comprising an organic solvent (butanol) dispersed in a continuous aqueous phase. Extraction with the second emulsion resulted in greater purity of isolated nucleic acid molecules relative to a traditional breaking method using repeated extractions with an organic extraction solvent.

The following reagents were used:
1-Butanol (non-water-saturated organic extraction solvent)
Recovery Solution (SDS Wash: 1×TE+0.1% SDS)
Wash Solution (TEX: 1×TE+0.1% TritonX-100)
PVC basin (VWR Cat# 21007-970) or AB collection plate w/96-well plate centrifuge
The nucleic acid-containing water-in-oil emulsion was collected into the PVC basin using an 8-channel pipette.

The emulsion was transferred using a pipette into six 1.5 mL tubes. (~1 mL per tube)

The emulsion was collected by spinning the tubes at 15,500 r.c.f. for 1 min. While the tubes were spinning, Breaking Solution was prepared as follows: 2.5 mL of Recovery Solution was added to 7.5 mL 1-butanol in a 15 mL tube. The breaking solution was vortexed for 1 min, forming a fine, white emulsified material, and vortexing was continued until no phase separation was visible.

After centrifugation, the clear top fraction of oil from the nucleic acid water-in-oil emulsion from each 1.5 mL tube was removed without disturbing the white emulsion phase at the bottom of the tube.

The breaking Solution was re-vortexed and pipetted in 1 mL aliquots into each of the 1.5 mL tubes containing the white emulsion obtained after centrifugation.

The resulting reaction mixture was vortexed for ~1 min to solubilize the bottom phase containing the white emulsion (from the water-in-oil emulsion) with the breaking solution.

The tubes were centrifuged at 15,500×g for 1 minute. After centrifugation, the tubes contained two clear phases, with minimal debris in the interface.

As much of the top organic solvent layer was removed as possible without disturbing the interface or the continuous aqueous phase.

1 mL of Recovery Solution was added to each 1.5 ml tube.

The tubes were vortexed for 1 min and centrifuged at 15,500×g for 3 minutes.

The supernatant was removed via pipetting from each tube, taking care to withdraw as much of the white emulsified oil layer as possible, and leaving ~50 µL in the bottom of each tube.

The remaining material from each tube was pooled into a new 1.5 mL tube as follows: 100 µL of Recovery Solution was added to each tube; each pellet within the tube was resuspended by pipetting up and down. All resuspended pellets were combined into a new 1.5 mL tube. Each tube was rinsed by pipetting in a single aliquot of 200 µL Recovery Solution and pipetting up and down in the bottom of the tube, then transferring this rinse to the next tube, and so on. Finally, the rinse was added to the new 1.5 mL tube containing the combined, resuspended pellets.

The new 1.5 mL tube containing the combined, resuspended pellets and rinse was vortexed for 1 min and centrifuged at 15,500×g for 3 min. The supernatant was removed by pipetting from top, taking care to remove as much white emulsified oil layer as best as possible, and leaving ~50 uL in bottom of the tube.

The following step was performed twice, for a total of two iterations: 1 mL of Wash Solution was added to the tube; the tube was vortexed for 1 min and centrifuged at 15,500×g for 3 minutes, and the supernatant removed by pipetting taking care to remove as much white emulsified oil layer as best as possible The resulting pellet was resuspended in 500 uL nuclease-free water or wash solution for longer-term storage.

Example 2

Breaking of a Water-in-Oil Emulsion Including Amplified Nucleic Acid Molecules in the Aqueous Phase, Using a Breaking Solution Comprising Octanol.

Reagents:
1-Octanol
Saturated N-Butanol (Prepared 20 minutes ahead of time by making a 50% v/v solution with Nuclease-Free Water)
Recovery Solution (as per Example 1)
Wash Solution (as per Example 1)

The water-in-oil emulsion including nucleic acid molecules in the aqueous phase was resuspended fully by pipetting the emulsion up and down in the wells using a multi-channel pipette equipped with LoBind tips.

The resuspended emulsion was transferred to a reservoir trough (Labcor Pipettor Solution Basins, Biotix, VWR Catalog #21007-970). The recovered emulsion was aliquoted into six 1.5 mL LoBind tubes. The tubes were centrifuged for 5 minutes at 15,500×g to pellet the emulsified sample. The supernatant was removed and discarded, leaving only a cloudy, white pellet behind.

10 mL of 1-octanol was poured into a fresh reservoir trough. 100 uL of 1-octanol was transferred to each well in the first column of the plate.

Using a multi-channel pipette equipped with the same LoBind tips used in the first step, the 1-octanol was pipetted up and down in the first column wells several times to fully rinse each well. The 1-octanol was then transferred from the first column to the second column of wells in the plate. The serial-transfer of the 1-octanol was repeated for each column in the plate. Once the 1-octanol was transferred into the last column, it was transferred into the emulsion reservoir trough. This rinsing step was repeated so that the wells of 96-well plate were each rinsed a total of two times with 100 uL of 1-octanol.

The walls of the emulsion reservoir trough were rinsed by pipetting the 1-octanol up and down several times.

The 1-octanol was aliquoted using a 1 mL pipette tip from the emulsion reservoir trough equally into the six 1.5 mL tubes containing the emulsion samples. Then, each of the six tubes was filled to the 1.5 mL mark with 1-octanol (~500-1000 uL). Each tube was vortexed at full speed until the white pellet was fully resuspended (~2-3 minutes). The tubes were rinsed for 3 minutes at 15,500×g. The top layer was removed and discarded from each tube while taking care not to disturb the interface.

Freshly prepared saturated N-butanol (1 mL) was added and vortexed at full speed to mix.

The tubes were vortexed for 3 minutes at 15,500×g.

The supernatant was withdrawn down to the interface while being careful not to disturb the interface and discarded.

1 mL of Recovery Solution was added to each 1.5 mL sample tube, following which the sample in each tube was resuspended by vortexing.

The tubes were vortexed for 3 minutes at 15,500×g.

The supernatant was withdrawn while leaving ~100 uL of solution in each 1.5 mL tube, without disturbing the pellet.

The remaining 100 uL of each sample was pipetted up and down to mix, and then all samples were transferred into a single, new 1.5 mL LoBind tube.

100 uL of Recovery Solution were added to each of the six 1.5 mL tubes, which were rinsed by pipetting the Recovery Solution up and down.

The recovery wash was transferred from each 1.5 mL tube to the new 1.5 mL tube containing all of the samples.

The tube containing the pooled samples was centrifuged for 3 minutes at 15,500×g.

The supernatant was removed and discarded, leaving behind approximately 20 uL to cover the pellet.

1 mL of Ion Wash Solution (Life Technologies, Part No. 4466463 (sold as a component of the Ion Template Solutions kit) was added to the tube, which was then vortexed to resuspend the pellet. The tube containing the pooled samples was centrifuged for 3 minutes at 15,500×g. The wash was repeated at least once, and in some trials up to three times.

The final pellet was resuspended in 100 uL of Ion Wash Solution (Life Technologies, Part No. 4466463 (sold as a component of the Ion Template Solutions kit).

Example 3

Reagents:
One 96-Well Plate Including Amplified Nucleic Acids Attached to Hydrogel Particles in Emulsion
Capture Beads: 10 ul MyOne™ C1 Streptavidin Magnetic beads (Dynal product; MyOne beads coated with Streptavidin)
High Salt Breaking Solution: 3:1; 3 volumes of 1-Butanol:1×PBS and 0.1% SDS in a final concentration of 35.2 mM inorganic salt (NaCl=34.5 mM and KCl=675 uM). Vortexed for 1 minute before use.
High Salt Recovery Solution: 1×PBS and 0.1% SDS in a final concentration of 140.7 mM inorganic salt (NaCl=138 mM and KCl=2.7 mM)
Wash Solution: Tris-HCL pH 7.6, and 0.1% Triton-X-100
Denaturation Solution: 125 mM NaOH and 0.1% Tween 20
Equipment
1.5 ml Eppendorf LoBind Tubes
ABI collection plate
Invitrogen DynaMag 2 magnet for 1.5 mL tubes
1.5 ml tube rotator
Protocol
The emulsion including amplified nucleic acids attached to hydrogel particles was collected from an emPCR plate using an ABI collection plate and by spinning for 4 minutes.
The emulsion was resuspended by pipetting up and down to mix, and was then dispensed into six 1.5 ml tubes
The tubes were centrifuged for 3 minutes at 15,500 rcf. The oil layer (clear, top supernatant) was removed.
A High Salt Breaking Solution was prepared as outlined in this example and vortexed for 30 sec to form an emulsion (i.e., until no phase separation was visible). 1 ml of the resulting high salt breaking solution was added to each tube, which was then vortexed thoroughly to solubilize the bottom phase containing the nucleic acids.
The tubes were centrifuged for 1 min at 15,500 rcf. The clear top supernatant was withdrawn as much as possible without disturbing the white interface.
1 ml of High Salt Recovery Solution was added to each sample, which was then vortexed thoroughly for at least 30 seconds.
The tubes were centrifuged for 1 min at 15,500 rcf. The supernatant (containing the white emulsified oil layer) was withdrawn, leaving behind approximately 50 ul.
The pellets in each of the six tubes were resuspended, pooled and combined into a clean tube. Each of the six tubes was rinsed in succession with the same 200 ul aliquot of High Salt Recovery Solution to capture all residual particles. This 200 ul rinse was added to the 300 ul pool previously collected.
10 ul of capture beads were added to the pooled sample. The beads were mixed with the sample by pipetting. The mixed sample was also vortexed for 1 minute. The pooled sample was attached to a tube rotator at room temperature for 10 minutes. After which, the tube containing the sample was placed on a DynaMag 2 magnet for 2 minutes in order to capture the beads.
After 2 minutes, the supernatant was removed and saved.
Wash Solution was added to the tube to a final total volume of 1000 uL. The sample was mixed well using a pipette, and the tube was replaced onto the DynaMag 2 magnet for an additional 2 minutes. The supernatant was removed and combined with the supernatant from the earlier corresponding step.
200 ul of denaturation solution was added to the supernatant and mixed well by pipetting. The sample was left to stand at room temperature for two minutes after which the tube was placed onto the DynaMag 2 magnet for 2 minutes. The supernatant was removed and placed on a clean tube.
500 ul of wash solution was added to the sample in the clean tube. The tube was vortexed for 30 seconds and then centrifuged for 3 min at 15,500 rcf.
The supernatant (containing the white emulsified oil layer) was removed to leave about 20 ul in the tube.
The pellet was resuspended in Wash Solution to a final volume of up to 100 uL and vortexed.
The resuspended sample was then stored long-term or used in any applicable downstream process.

What is claimed:

1. A method for breaking a water-in-oil emulsion including one or more biomolecules dispersed in an aqueous phase of the water-in-oil emulsion, comprising:
   a) obtaining a first emulsion which contains a plurality of aqueous droplets in a continuous hydrophobic fraction, wherein the plurality of aqueous droplets include one or more biomolecules, wherein the one or more biomolecules are attached to beads or particles, and wherein the one or more biomolecules comprises polynucleotides or polypeptides;
   b) breaking the first emulsion by mixing the first emulsion with 1-octanol to form a first mixture;
   c) centrifuging the first mixture to form a top phase, an interface and a bottom phase;
   d) removing and the top phase of step (c) and retaining the interface and bottom phase;
   e) mixing the interface and bottom phase with N-butanol to form a second mixture;
   f) centrifuging the second mixture to form a top phase, an interface and a bottom phase; and
   g) removing the top phase of step (f) and retaining the interface and bottom phase, wherein the bottom phase contains the one or more biomolecules.

2. The method of claim 1, further comprising: isolating the one or more biomolecules from the retained bottom phase of step (g), by contacting the retained bottom phase with an aqueous recovery solution which contains sodium dodecyl sulfate (SDS), or saline-sodium citrate (SSC).

3. The method of claim 1, further comprising: sequencing the one or more of the polypeptides.

4. The method of claim 1, further comprising: sequencing the one or more of the polynucleotides.

5. The method of claim 4, wherein the sequencing the polynucleotides comprises: disposing the one or more polynucleotides into a plurality of reaction chambers arranged in an array, wherein the reaction chambers are coupled to at least one ion sensor that detects protons.

6. The method of claim 5, wherein the at least one ion sensor comprises a field effect transistor (FET).

7. The method of claim 4, wherein the sequencing comprises conducting a primer extension reaction with a polymerase and nucleotides.

8. The method of claim 5, wherein the sequencing comprises conducting a primer extension reaction, by contacting a polymerase with the one or more polynucleotides that are disposed into the plurality of the reaction chambers, and flowing a plurality of nucleotides into the plurality of reaction chambers.

9. The method of claim 1, wherein the continuous hydrophobic fraction in step (a) includes oil.

10. The method of claim 9, wherein the oil is selected from the group consisting of mineral oil, silicone based oil or fluorinated oils.

11. The method of claim 1, wherein the plurality of aqueous droplets include an inorganic salt.

12. The method of claim 11, wherein the inorganic salt is selected from the group consisting of potassium chloride, sodium chloride, lithium chloride, $Na_2SO_4$, potassium carbonate and ammonium sulfate.

13. The method of claim 1, wherein individual droplets, of the plurality of droplets, contains 1-10 biomolecules.

14. The method of claim 1, wherein the polynucleotides include single-stranded or double-stranded polynucleotides.

15. The method of claim 1, where the polynucleotides include RNA, DNA, cDNA, genomic DNA or mRNA.

16. The method of claim 1, wherein the polypeptide is selected from the group consisting of: enzymes, antibodies, hormones and antigens.

\* \* \* \* \*